United States Patent
Bateman et al.

(10) Patent No.: US 12,036,114 B2
(45) Date of Patent: Jul. 16, 2024

(54) STENTED PROSTHETIC HEART VALVE HAVING A WRAP AND DELIVERY DEVICES

(71) Applicant: Medtronic Vascular, Inc., Santa Rosa, CA (US)

(72) Inventors: Michael Bateman, St. Louis Park, MN (US); Cynthia Clague, Minnetonka, MN (US); Jeffrey Sandstrom, Scandia, MN (US); Joel Racchini, Edina, MN (US); James R. Keogh, Maplewood, MN (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 253 days.

(21) Appl. No.: 17/116,431

(22) Filed: Dec. 9, 2020

(65) Prior Publication Data

US 2021/0085455 A1  Mar. 25, 2021

Related U.S. Application Data

(62) Division of application No. 15/458,387, filed on Mar. 14, 2017, now Pat. No. 10,888,420.

(Continued)

(51) Int. Cl.
*A61F 2/24* (2006.01)
*A61F 2/844* (2013.01)
*A61F 2/852* (2013.01)

(52) U.S. Cl.
CPC .......... *A61F 2/2418* (2013.01); *A61F 2/2409* (2013.01); *A61F 2/2436* (2013.01);
(Continued)

(58) Field of Classification Search
CPC .... A61F 2/2409; A61F 2/2418; A61F 2/2439; A61F 2/2436; A61F 2/844
See application file for complete search history.

(56) References Cited

U.S. PATENT DOCUMENTS

| 5,035,706 A | 7/1991 | Giantureo et al. |
| 5,335,398 A | 8/1994 | Schottker et al. |

(Continued)

FOREIGN PATENT DOCUMENTS

| CN | 103705315 | 4/2014 |
| EP | 0537487 | 4/1993 |

(Continued)

OTHER PUBLICATIONS

The International Search Report and Written Opinion for International Application No. PCT/US2014/014090 mailed Apr. 14, 2014 (11 pages).

(Continued)

*Primary Examiner* — Alexander J Orkin
(74) *Attorney, Agent, or Firm* — Wentsler LLC

(57) ABSTRACT

Stented prosthetic heart valves comprising a stent frame having a compressed arrangement for delivery within a patient's vasculature and an expanded arrangement for deployment within a native heart valve. The stented prosthetic heart valves including a paravalvular leakage prevention or mitigation wrap that encircles a stent frame and is formed of a flexible material having a variable diameter defined by a greatest distance between the wrap and the stent frame. The wrap further includes a first end coupled to the stent frame and an opposing second end that is not coupled to the stent frame, wherein the wrap can selectively enlarge its diameter in situ via movement of the second end. Devices for and methods of selectively deploying the wrap are also disclosed.

16 Claims, 8 Drawing Sheets

Related U.S. Application Data

(60) Provisional application No. 62/307,665, filed on Mar. 14, 2016.

(52) U.S. Cl.
CPC ............ *A61F 2/2439* (2013.01); *A61F 2/844* (2013.01); *A61F 2/852* (2013.01); *A61F 2220/0025* (2013.01); *A61F 2220/0033* (2013.01); *A61F 2250/0069* (2013.01)

(56) References Cited

U.S. PATENT DOCUMENTS

| | | |
|---|---|---|
| 5,571,175 A | 11/1996 | Vanney et al. |
| 5,693,084 A | 12/1997 | Chuter |
| 5,776,186 A | 7/1998 | Uflacker |
| 5,957,949 A | 9/1999 | Leonhardt et al. |
| 6,280,465 B1 | 8/2001 | Cryer |
| 6,517,550 B1 | 2/2003 | Konya et al. |
| 6,733,521 B2 | 5/2004 | Chobotov et al. |
| 6,740,111 B1 | 5/2004 | Lauterjung |
| 7,033,390 B2 | 4/2006 | Johnson et al. |
| 7,044,966 B2 | 5/2006 | Svanidze et al. |
| 7,276,078 B2 | 10/2007 | Spenser et al. |
| 7,329,275 B2 | 2/2008 | Yee |
| 7,329,279 B2 | 2/2008 | Haug et al. |
| 7,331,991 B2 | 2/2008 | Kheradvar et al. |
| 7,445,631 B2 | 11/2008 | Salahieh et al. |
| 7,503,929 B2 | 3/2009 | Johnson et al. |
| 7,524,331 B2 | 4/2009 | Birdsall |
| 7,534,261 B2 | 5/2009 | Friedman |
| 7,628,805 B2 | 12/2009 | Spenser et al. |
| 7,708,775 B2 | 5/2010 | Rowe et al. |
| 7,780,725 B2 | 8/2010 | Haug et al. |
| 7,972,378 B2 | 7/2011 | Tabor et al. |
| 8,002,825 B2 | 8/2011 | Letac et al. |
| 8,142,497 B2 | 3/2012 | Friedman |
| 8,182,528 B2 | 5/2012 | Salahieh et al. |
| 8,231,670 B2 | 7/2012 | Salahieh et al. |
| 8,246,678 B2 | 8/2012 | Salahieh et al. |
| 8,252,052 B2 | 8/2012 | Salahieh et al. |
| 8,403,981 B2 | 3/2013 | Forster et al. |
| 8,449,599 B2 | 5/2013 | Chau et al. |
| 8,603,160 B2 | 12/2013 | Salahieh et al. |
| 8,623,078 B2 | 1/2014 | Salahieh et al. |
| 8,628,566 B2 | 1/2014 | Eberhardt et al. |
| 8,641,757 B2 | 2/2014 | Pintor et al. |
| 8,668,733 B2 | 3/2014 | Salahieh et al. |
| 8,673,000 B2 | 3/2014 | Tabor et al. |
| 8,734,484 B2 | 5/2014 | Ahlberg et al. |
| 8,795,357 B2 | 8/2014 | Yohanan et al. |
| 8,801,706 B2 | 8/2014 | Rothstein et al. |
| 8,801,776 B2 | 8/2014 | House et al. |
| 8,808,356 B2 | 8/2014 | Braido et al. |
| 8,840,662 B2 | 9/2014 | Salahieh et al. |
| 8,840,663 B2 | 9/2014 | Salahieh et al. |
| 8,852,272 B2 | 10/2014 | Gross et al. |
| 8,926,690 B2 | 1/2015 | Kovalsky |
| 8,986,371 B2 | 3/2015 | Quill et al. |
| 8,986,375 B2 | 3/2015 | Garde et al. |
| 8,992,608 B2 | 3/2015 | Haug et al. |
| 9,011,521 B2 | 4/2015 | Haug et al. |
| 9,675,451 B2 | 6/2017 | Garde et al. |
| 9,974,649 B2 | 5/2018 | Racchini et al. |
| 10,179,045 B2 | 1/2019 | Racchini et al. |
| 10,888,420 B2 | 1/2021 | Bateman et al. |
| 2003/0199963 A1 | 10/2003 | Tower et al. |
| 2003/0199971 A1 | 10/2003 | Tower et al. |
| 2004/0030381 A1 | 2/2004 | Shu |
| 2004/0111111 A1 | 6/2004 | Lin |
| 2004/0122514 A1 | 6/2004 | Fogarty et al. |
| 2005/0119722 A1 | 6/2005 | Styrc et al. |
| 2005/0137690 A1* | 6/2005 | Salahieh .............. A61F 2/2427 623/1.36 |
| 2005/0137695 A1 | 6/2005 | Salahieh et al. |
| 2006/0004442 A1 | 1/2006 | Spenser et al. |
| 2007/0016285 A1 | 1/2007 | Lane et al. |
| 2007/0244544 A1 | 10/2007 | Birdsall et al. |
| 2007/0270944 A1 | 11/2007 | Bergheim et al. |
| 2007/0293944 A1 | 12/2007 | Spenser et al. |
| 2008/0243245 A1 | 10/2008 | Thambar et al. |
| 2008/0275540 A1 | 11/2008 | Wen |
| 2009/0099653 A1 | 4/2009 | Suri et al. |
| 2009/0112311 A1 | 4/2009 | Miles et al. |
| 2009/0192591 A1 | 7/2009 | Ryan et al. |
| 2010/0036479 A1 | 2/2010 | Hill et al. |
| 2010/0168844 A1 | 7/2010 | Toomes et al. |
| 2010/0198238 A1 | 8/2010 | Sorajja |
| 2010/0280589 A1 | 11/2010 | Styrc |
| 2010/0286768 A1 | 11/2010 | Alkhatib |
| 2011/0040366 A1 | 2/2011 | Goetz et al. |
| 2011/0054466 A1 | 3/2011 | Rothstein et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0245911 A1 | 10/2011 | Quill et al. |
| 2011/0257721 A1 | 10/2011 | Tabor |
| 2011/0264206 A1 | 10/2011 | Tabor |
| 2012/0022633 A1 | 1/2012 | Olson et al. |
| 2012/0041549 A1 | 2/2012 | Salahieh et al. |
| 2012/0041550 A1 | 2/2012 | Salahieh et al. |
| 2012/0123529 A1 | 5/2012 | Levi et al. |
| 2012/0277734 A1 | 11/2012 | Goetz et al. |
| 2013/0030519 A1 | 1/2013 | Tran et al. |
| 2013/0190857 A1 | 7/2013 | Mitra et al. |
| 2013/0190862 A1 | 7/2013 | Pintor et al. |
| 2013/0197622 A1 | 8/2013 | Mitra et al. |
| 2013/0245752 A1 | 9/2013 | Goetz et al. |
| 2013/0245753 A1 | 9/2013 | Alkhatib |
| 2013/0274873 A1 | 10/2013 | Delaloye et al. |
| 2013/0331929 A1 | 12/2013 | Mitra et al. |
| 2013/0338755 A1 | 12/2013 | Goetz et al. |
| 2013/0338765 A1 | 12/2013 | Braido et al. |
| 2014/0046426 A1 | 2/2014 | Kovalsky |
| 2014/0094904 A1 | 4/2014 | Salahieh et al. |
| 2014/0107772 A1 | 4/2014 | Li et al. |
| 2014/0114402 A1 | 4/2014 | Ahlberg et al. |
| 2014/0114406 A1 | 4/2014 | Salahieh et al. |
| 2014/0194975 A1 | 7/2014 | Quill et al. |
| 2014/0194981 A1 | 7/2014 | Menk et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0243969 A1 | 8/2014 | Venkatasubramanian et al. |
| 2014/0257475 A1 | 9/2014 | Gross et al. |
| 2014/0277388 A1 | 9/2014 | Skemp |
| 2014/0277413 A1 | 9/2014 | Richter et al. |
| 2014/0277417 A1 | 9/2014 | Schraut et al. |
| 2014/0277419 A1 | 9/2014 | Garde et al. |
| 2014/0277422 A1 | 9/2014 | Ratz et al. |
| 2014/0277423 A1 | 9/2014 | Alkhatib et al. |
| 2014/0277424 A1 | 9/2014 | Oslund |
| 2014/0277425 A1 | 9/2014 | Dakin |
| 2014/0277426 A1 | 9/2014 | Dakin et al. |
| 2014/0277428 A1 | 9/2014 | Skemp et al. |
| 2014/0296975 A1 | 10/2014 | Tegels et al. |
| 2014/0316516 A1 | 10/2014 | Vidlund et al. |
| 2014/0330368 A1 | 11/2014 | Gloss et al. |
| 2014/0343671 A1 | 11/2014 | Yohanan et al. |
| 2014/0350663 A1 | 11/2014 | Braido et al. |
| 2014/0350665 A1 | 11/2014 | Braido et al. |
| 2014/0350667 A1 | 11/2014 | Braido et al. |
| 2014/0350668 A1 | 11/2014 | Delaloye et al. |
| 2014/0371844 A1 | 12/2014 | Dale et al. |
| 2015/0005863 A1 | 1/2015 | Para |
| 2015/0073540 A1 | 3/2015 | Salahieh et al. |
| 2015/0073541 A1 | 3/2015 | Salahieh et al. |
| 2015/0073544 A1 | 3/2015 | Gormann, III et al. |
| 2015/0073548 A1 | 3/2015 | Mattheny |
| 2015/0112430 A1 | 4/2015 | Creaven et al. |
| 2015/0122687 A1 | 5/2015 | Zeng et al. |
| 2015/0127098 A1 | 5/2015 | Braido et al. |
| 2015/0142100 A1 | 5/2015 | Morriss et al. |
| 2015/0142103 A1 | 5/2015 | Vidlund |

(56) References Cited

U.S. PATENT DOCUMENTS

| | | |
|---|---|---|
| 2015/0142104 A1 | 5/2015 | Braido |
| 2015/0148898 A1 | 5/2015 | Krivoruchko et al. |
| 2015/0157455 A1 | 6/2015 | Hoang et al. |
| 2015/0209136 A1 | 7/2015 | Braido et al. |
| 2015/0216654 A1 | 8/2015 | Braido et al. |
| 2015/0216663 A1 | 8/2015 | Braido et al. |
| 2015/0238315 A1 | 8/2015 | Rabito et al. |
| 2015/0245909 A1 | 9/2015 | Salahieh et al. |
| 2015/0327995 A1 | 11/2015 | Morin et al. |
| 2015/0327996 A1 | 11/2015 | Fahim et al. |

FOREIGN PATENT DOCUMENTS

| | | |
|---|---|---|
| EP | 1758523 | 1/2006 |
| EP | 2674130 | 3/2016 |
| WO | WO2009094501 | 7/2009 |
| WO | WO2011051043 | 5/2011 |
| WO | WO2013033791 | 3/2013 |
| WO | WO2013059747 | 4/2013 |
| WO | WO2014/072439 | 5/2014 |
| WO | WO2015/152980 | 10/2015 |

OTHER PUBLICATIONS

PCT/US2017/022285, The International Search Report and the Written Opinion of the International Searching Authority, mailed Apr. 26, 2017.

\* cited by examiner

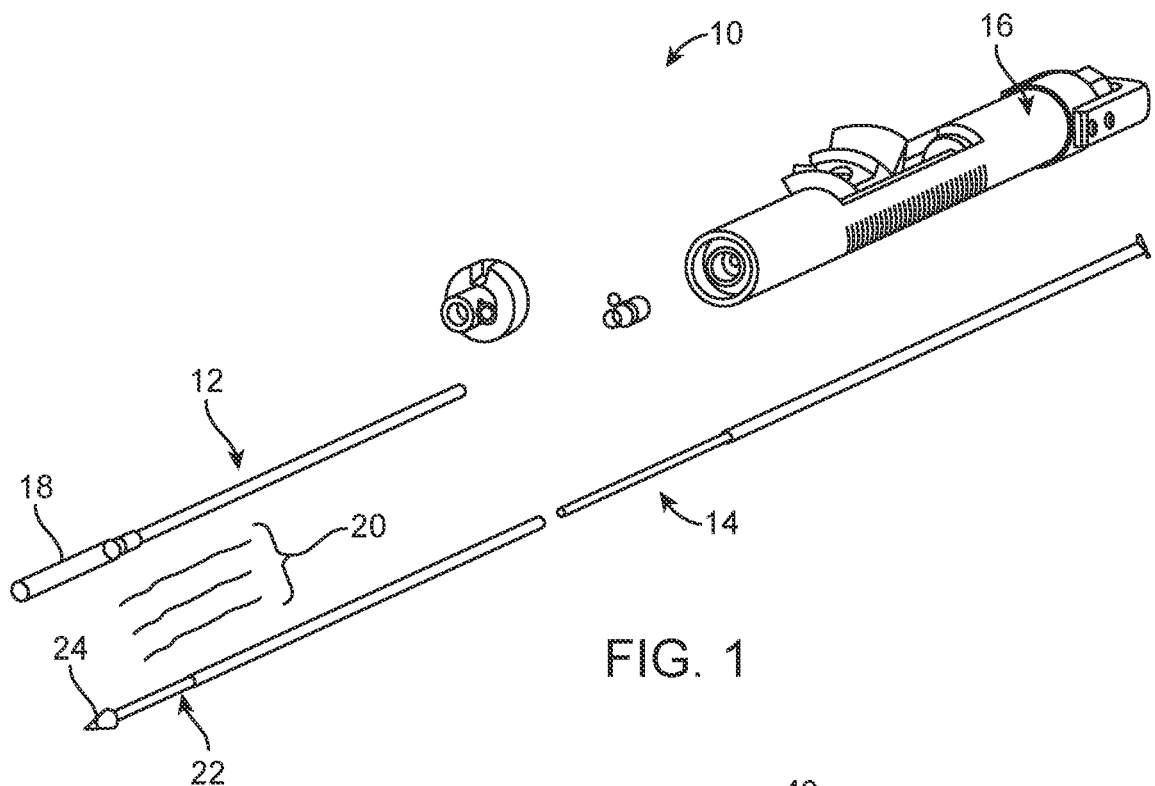
FIG. 1
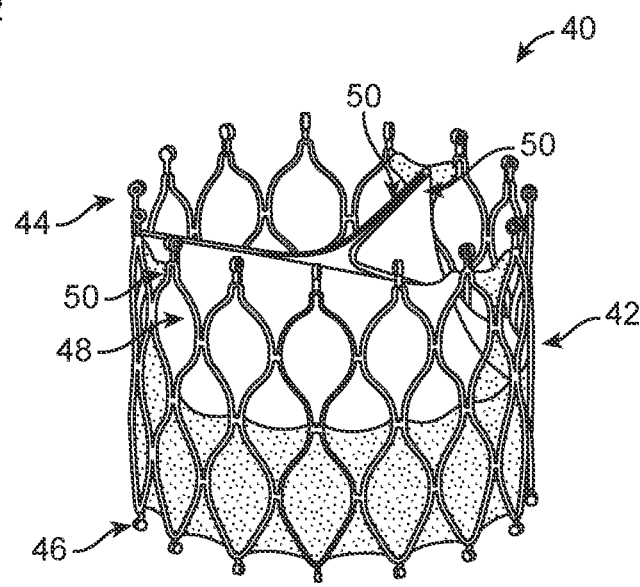
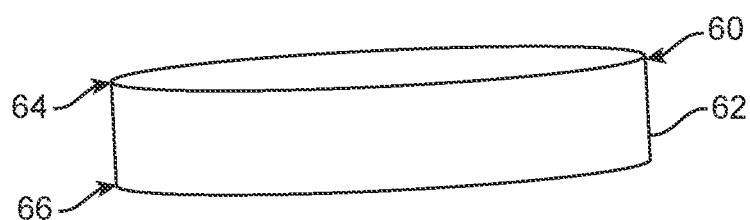
FIG. 2

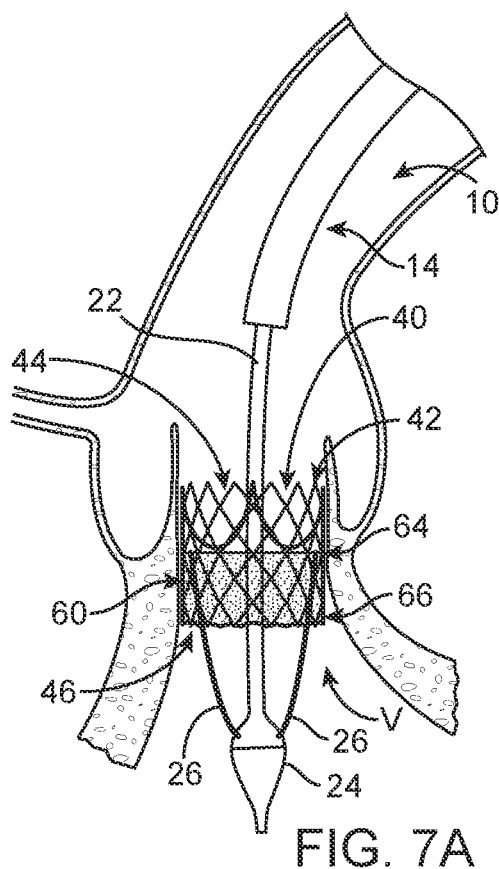
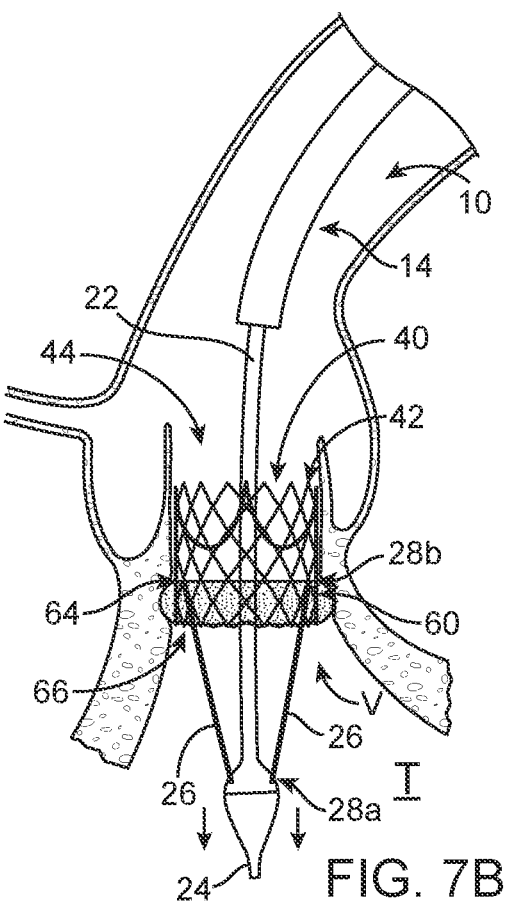
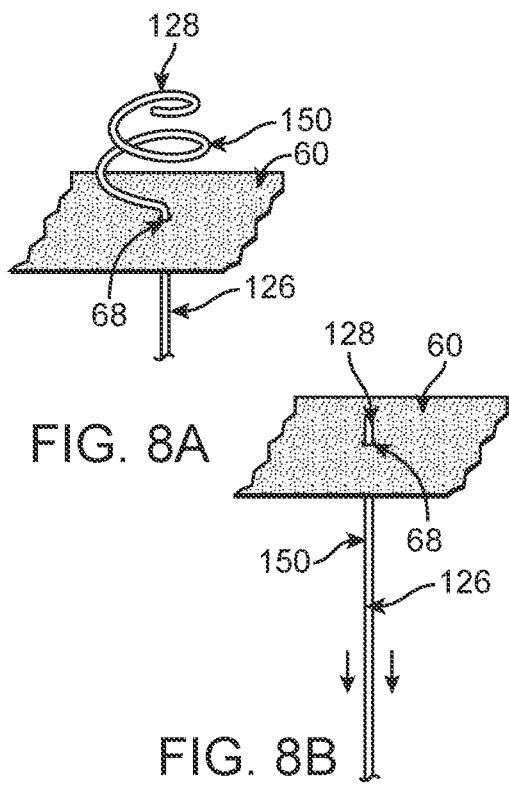
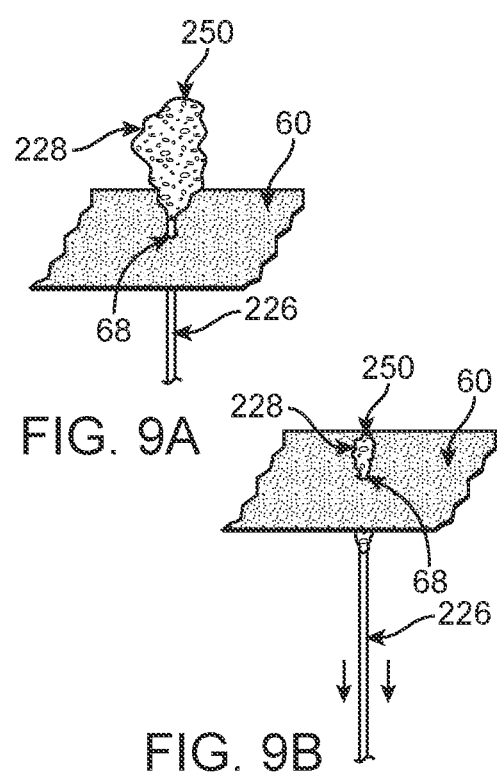

STENTED PROSTHETIC HEART VALVE HAVING A WRAP AND DELIVERY DEVICES

CROSS-REFERENCE TO RELATED APPLICATIONS

This application is a Divisional application of Ser. No. 15/458,387, filed on Mar. 14, 2017, entitled, "STENTED PROSTHETIC HEART VALVE HAVING A WRAP AND DELIVERY DEVICES," now allowed, which claims the benefit of the filing date of U.S. Provisional Patent Application Ser. No. 62/307,665, filed Mar. 14, 2016, entitled "STENTED PROSTHETIC HEART VALVE HAVING A WRAP AND DELIVERY DEVICES," the entire teachings of which are incorporated herein by reference.

BACKGROUND

The present disclosure relates to stented prosthetic heart valves having a paravalvular leakage prevention or mitigation wrap, as well as delivery devices and methods for selectively deploying the wrap.

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent." Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement prosthetic valve is delivered in a compressed condition to the valve site, where it is expanded to its operational state within the native valve. Calcified or diseased native leaflets are pressed to the side walls of the native valve by the radial force of the stent frame of the prosthetic valve. These calcified leaflets can lead to incomplete conformance of the stent frame with the native valve and can be a source of paravalvular leakage ("PVL"). Significant pressure gradients across the valve cause blood to leak through the gaps between the implanted prosthetic valve and the calcified anatomy. When present, such paravalvular leakage is highly detrimental to the patient.

The present disclosure addresses problems and limitations associated with the related art.

SUMMARY

As discussed above, stented prosthetic heart valves can leave paravalvular leakage pathways in some patients, particularly patients with very immobile or heavily calcified native valve leaflets. Disclosed embodiments include stented prosthetic heart valves having a stent frame with a wrap that can be optionally deployed, if paravalvular leakage is detected, to fill commissural paravalvular leakage pathways. In other words, the arrangement of the wrap is controlled independently of the configuration (i.e. expansion) of the stent frame. The wrap includes a body of flexible material positioned around an end of the stent frame. In disclosed embodiments, the wrap is configured so that in a deployed position, the wrap bulges outwardly from the stent frame as one end of the wrap is positioned closer to a second, opposing end of the wrap.

Actuation of the wrap can be accomplished in a variety of ways. For example, the delivery device can include a plurality of tethers that are connected to both a movable end of the wrap and a shaft assembly of the delivery device. The shaft assembly is configured to selectively position the tethers and, thus the wrap. Once the wrap is in the deployed position, coupling elements can be utilized to maintain the deployed position of the wrap. Exemplary coupling elements include a ratchet, hooks and barbs. In other embodiments, the wrap is constructed to be biased in the deployed position and will generally remain in the deployed position once forces overcoming the natural bias to maintain the wrap in the delivery position are released.

After the wrap is maintained in the deployed position and the stented prosthetic heart valve hemodynamics and paravalvular leakage are assessed and deemed acceptable, the delivery device is disengaged from the wrap and the stented prosthetic heart valve so that the delivery device can be retracted from the patient.

BRIEF DESCRIPTION OF THE DRAWINGS

FIG. 1 is a perspective view of an illustrative delivery device.

FIG. 2 is a partially exploded view of a stented prosthetic heart valve that can be delivered with the delivery device of FIG. 1; the stented prosthetic heart valve having a stent frame in an expanded arrangement.

wherein the stent frame is in the expanded arrangement and the wrap is in the delivery position.

Figure 5A:
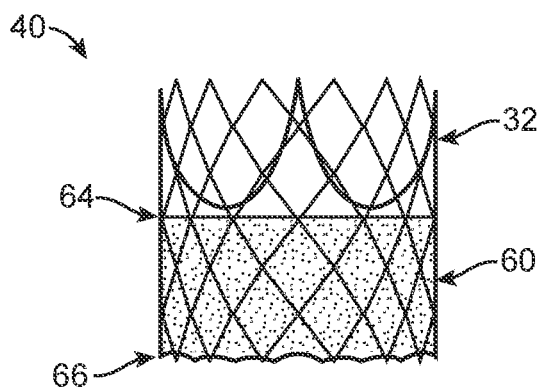
FIG. 5A is a schematic side view of the stented prosthetic heart valve of FIG. 2, in the expanded arrangement; the stented prosthetic heart valve having a wrap in a delivery position.
Figure 5B:
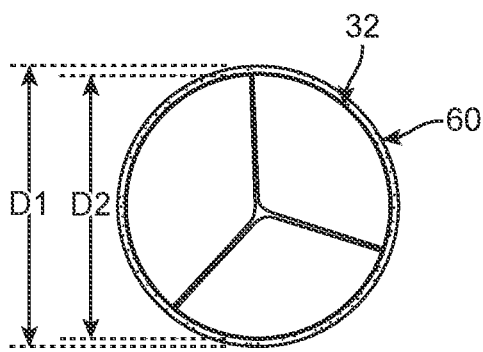
FIG. 5B is a schematic profile view of the stented prosthetic heart valve of FIG. 5A.
Figure 5C:
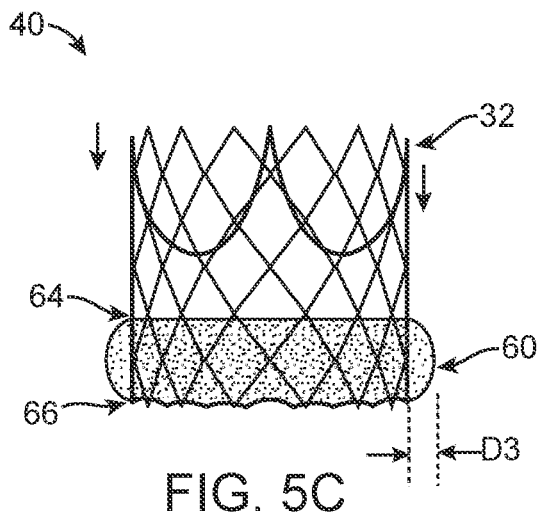

FIG. 5C is a partial, schematic side view of the stented prosthetic heart valve of FIGS. 5A-5B, in which the stent frame is in the expanded arrangement and the wrap is in a deployed position.

Figure 5D:
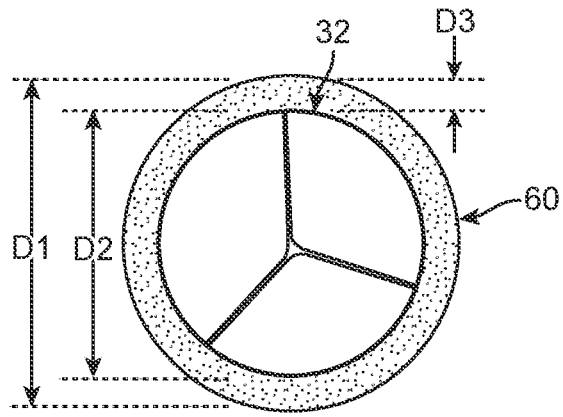

FIG. 5D is a schematic profile view of the stented prosthetic heart valve of FIG. 5C; wherein the stent frame is in the expanded arrangement and the wrap is in the deployed position.

Figure 6A:
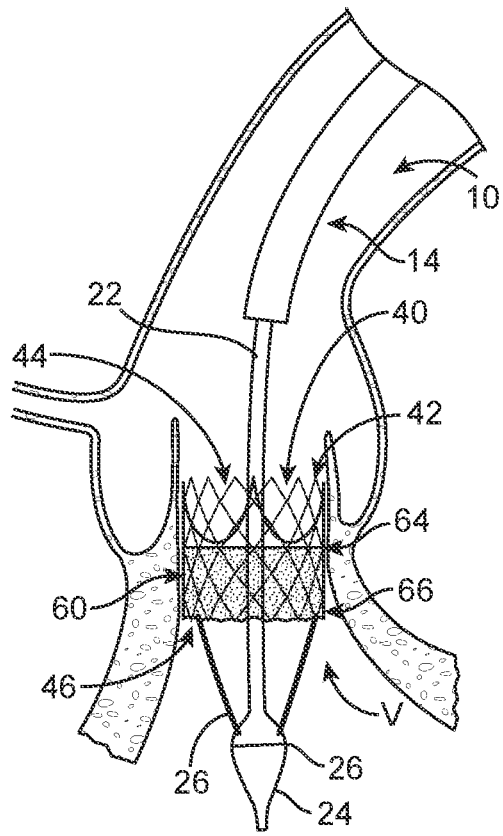

FIG. 6A is a partial, schematic view of one way in which the delivery device of FIG. 1 can be modified to deliver the stented prosthetic heart valve of FIG. 2; wherein the wrap is in the delivery position.

Figure 6B:
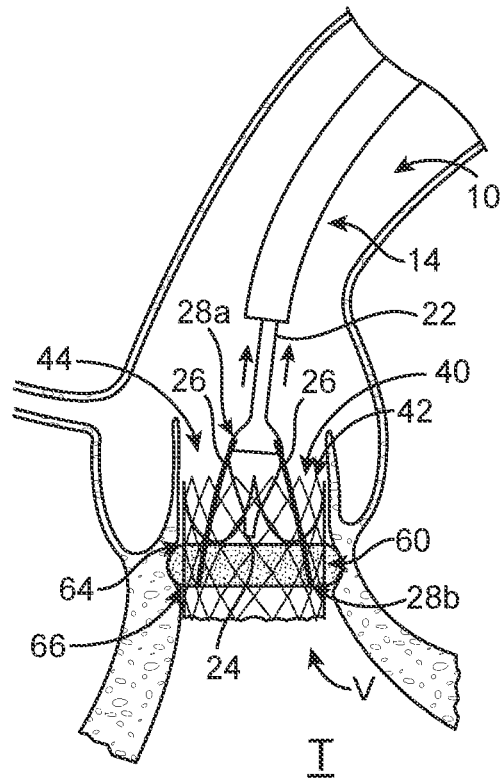

FIG. 6B is a partial, schematic view of the delivery device of FIG. 1; wherein the wrap is deployed with a plurality of tethers of the delivery device by pulling a distal end of the wrap proximally.

FIG. 7A is a partial, schematic view of another way in which the delivery device of FIG. 1 can be modified to deliver the stented prosthetic heart valve of FIG. 2; wherein the wrap is in the delivery position.

FIG. 7B is a partial, schematic view of the delivery device of FIG. 7A; wherein the wrap is deployed with the plurality of tethers of the delivery device by pulling or pushing a proximal end of the wrap distally.

FIG. 8A is a partial, schematic illustration of one tether, similar to the tethers of FIGS. 6A-7B, the tether having a pigtail curve that can releasably secure the tether to the wrap.

FIG. 8B is a partial, schematic illustration of the pigtail curve of FIG. 8A having tension applied thereto in order to straighten the pigtail curve for release through an aperture in the wrap.

FIG. 9A is a partial, schematic illustration of an alternate tether, similar to those previously disclosed, the tether having a compressible section that can releasably secure the tether to the wrap.

FIG. 9B is a partial, schematic illustration of the compressible section of FIG. 9A having tension applied thereto in order to compress the compressible section for release of the tether through the aperture in the wrap.

Figure 10A:
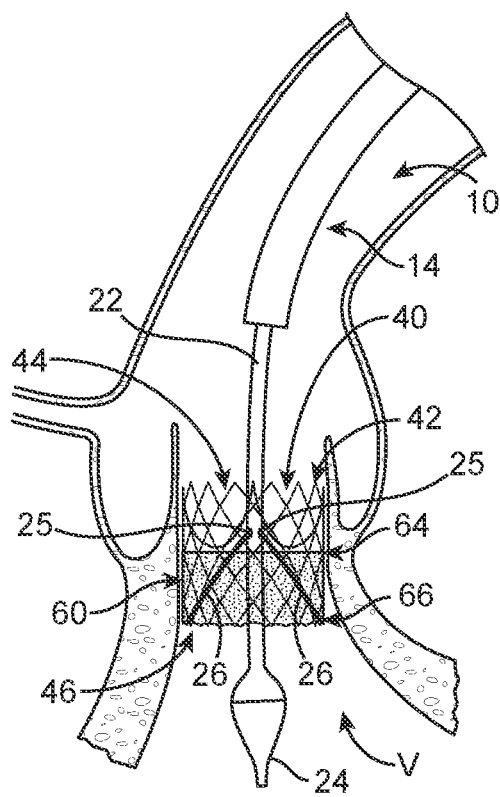

FIG. 10A is a partial, schematic illustration of another way in which the delivery device of FIG. 1 can be modified to deliver the stented prosthetic heart valve of FIG. 2; wherein the wrap is in the delivery position.

Figure 10B:
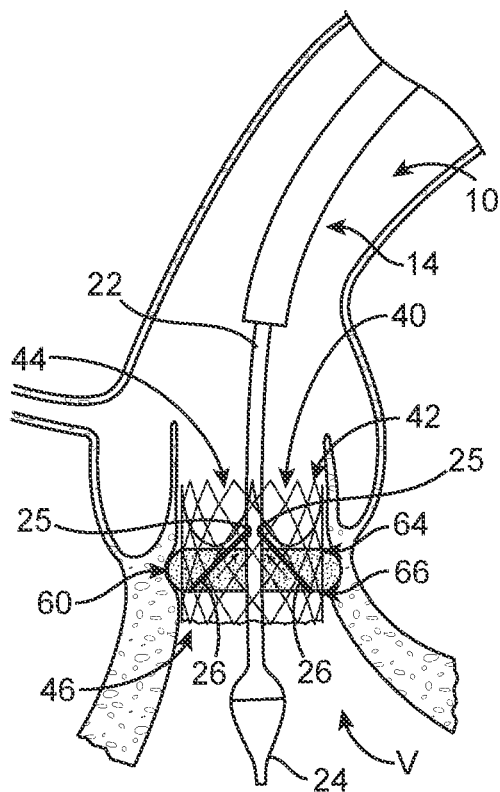

FIG. 10B is a partial, schematic view of the delivery device of FIG. 10A; wherein the wrap is deployed with the plurality of tethers that are actuated with a handle assembly (see also, FIG. 1).

Figure 11A:
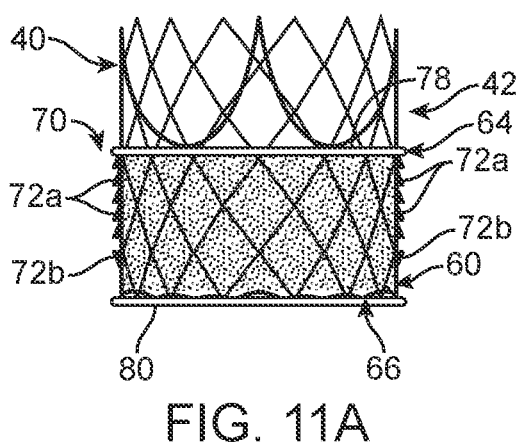

FIG. 11A is a schematic illustration of a ratchet system that can be used to retain the wrap in the deployed position; wherein the wrap has not yet been deployed.

Figure 11B:
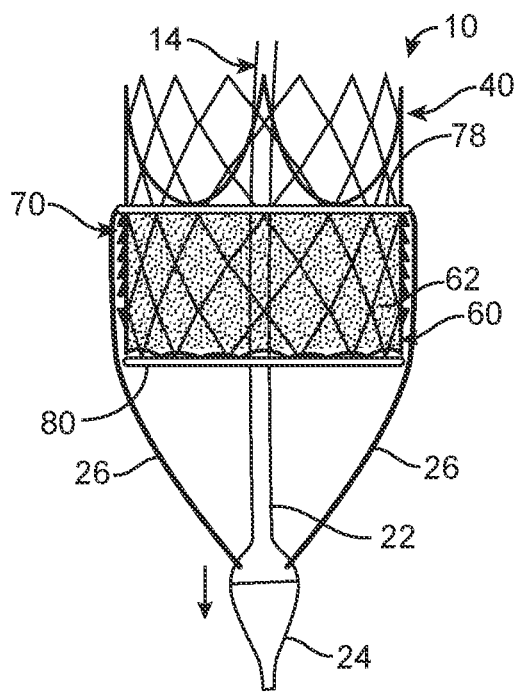

FIG. 11B is schematic illustration of the ratchet system of FIG. 11A in relation to the delivery device; wherein the wrap has not yet been deployed.

Figure 11C:
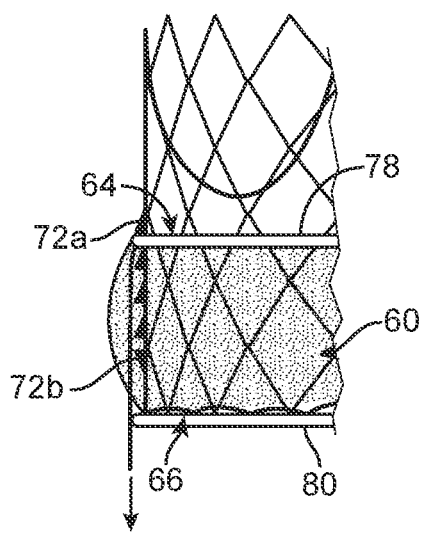

FIG. 11C is a schematic illustration of the wrap of FIGS. 11A-11B in a partially-deployed position.

Figure 11D:
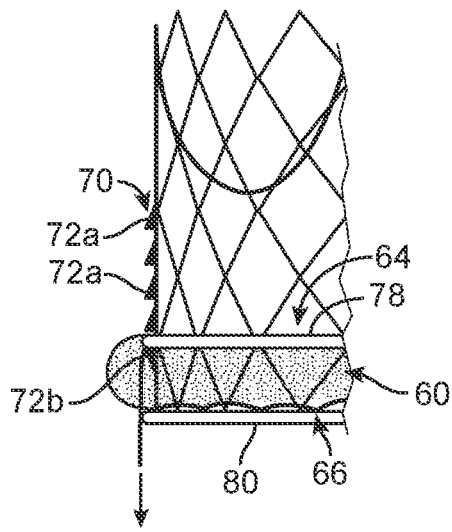

FIG. 11D is a schematic illustration of the wrap in the deployed position.

Figure 11E:
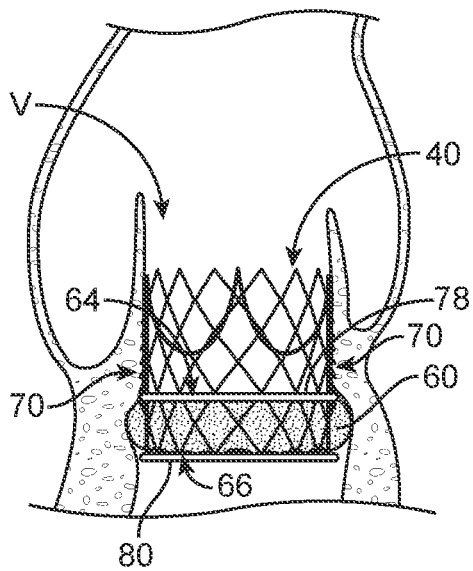

FIG. 11E is a schematic illustration of the wrap deployed within the native heart valve.

Figure 12A:
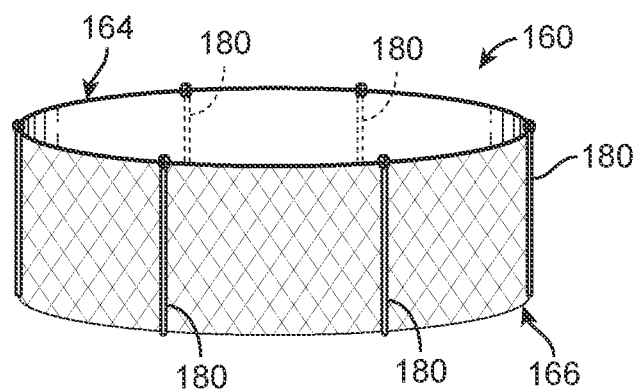

FIG. 12A is a schematic illustration of an alternate wrap design in a delivery position.

Figure 12B:
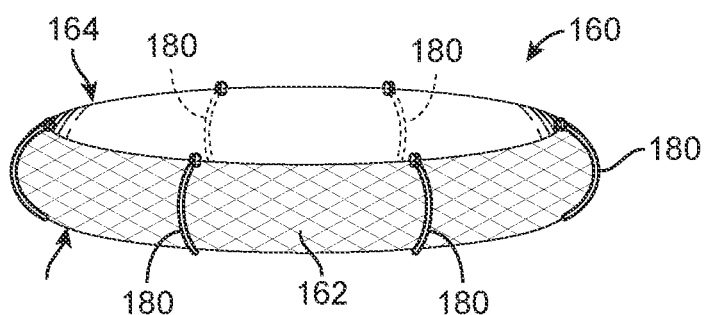

FIG. 12B is a schematic illustration of the wrap of FIG. 12A in a deployed position; wherein the wrap is biased in the deployed position with a plurality of spines.

Figure 12C:
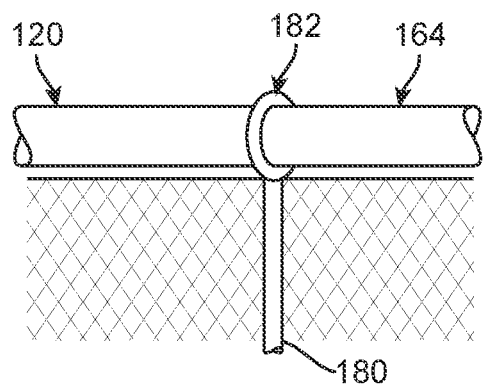

FIG. 12C is partial, a schematic illustration of one spine of FIGS. 12A-12B connected to a tension member circumscribing the wrap.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Certain aspects of the present disclosure relate to transcatheter stented prosthetic heart valve delivery devices that retain a stented prosthetic heart valve (hereinafter "prosthetic valve") in a compressed arrangement during delivery to a target site and allow the prosthetic valve to expand and deploy at a target site. By way of background, general components of one non-limiting example of a delivery device 10 with which the aspects of the present disclosure are useful is illustrated in FIG. 1. The delivery device 10 is arranged and configured for percutaneously delivering a prosthetic valve (e.g., the prosthetic valve 40 of FIG. 2) to a patient's defective heart valve (see also, FIGS. 4A-4B). The delivery device 10 includes an optional outer sheath assembly 12, a shaft assembly 14, and a handle assembly 16. The shaft assembly 14 includes a distal portion 22 and terminates at a tip 24. Where provided, the optional outer sheath assembly 12 includes a capsule 18 selectively disposed over the prosthetic valve 40 that sheathes the prosthetic valve 40 in the loaded or compressed arrangement and can be retracted by the handle assembly 16 to expose the prosthetic valve 40, thus allowing the prosthetic valve 40 to expand. In some constructions, the capsule 18 and the outer sheath assembly 12 are comprised of differing materials and/or constructions, with the capsule 18 having a longitudinal length approximating (e.g., slightly greater than) a length of the prosthetic valve 40 to be used with the delivery device 10. A material and thickness of the capsule 18 is selected to exhibit sufficient radial rigidity so as to overtly resist the expected expansive forces of the prosthetic valve 40 when compressed within the capsule 18. However, the capsule 18 exhibits sufficient longitudinal flexibility for ready passage through a patient's vasculature and into the native heart valve to be replaced.

One or more elongate tension members 20 can optionally be provided to constrain and compress the prosthetic valve 40. Suitable elongate tension members, include, but are not limited to sutures, chords, wires or filaments. The tension member(s) 20 can be considered part of the delivery device 10 in some embodiments or as part of the prosthetic valve 40 in other embodiments. The delivery device 10 provides a loaded delivery state (FIG. 3A) in which the prosthetic valve 40 is loaded over the shaft assembly 14 and is compressively retained on the distal portion 22 by the tension members 20. In some embodiments, compression of the prosthetic valve 40 is maintained and adjusted with the tension members 20. Once the loaded and compressed prosthetic valve 40 is located at a target site, tension in the tension members 20 is lessened or released to permit the prosthetic valve 40 to self-expand, partially releasing and ultimately fully deploying the prosthetic valve 40 from the shaft assembly 14. The tension members 20, if provided, can be configured to be released from the prosthetic valve 40 with the handle assembly 16 or the like. After deployment of the prosthetic valve 40 at the target site, paravalvular leakage can occur. Therefore, delivery devices 10 disclosed herein are configured to selectively actuate a paravalvular leakage prevention wrap 60 of the prosthetic valve 40, as will be discussed in further detail below.

Figure 3A:
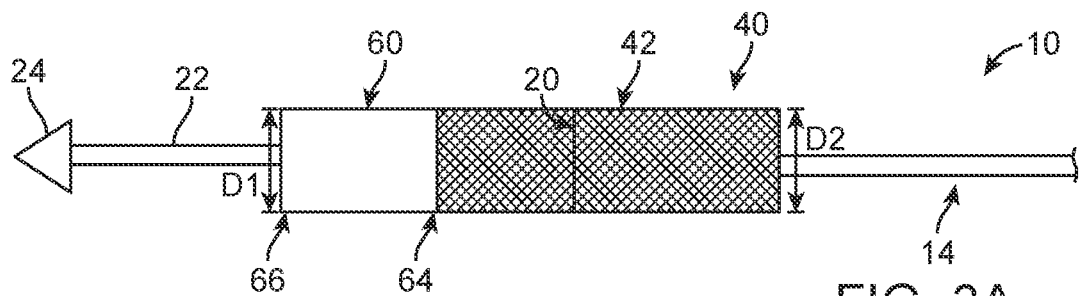
FIG. 3A is a schematic illustration of part of the delivery device of FIG. 1 having the stented prosthetic heart valve of FIG. 2 loaded thereto in a compressed arrangement; the stented prosthetic heart valve including a wrap in a delivery position.
Figure 3B:
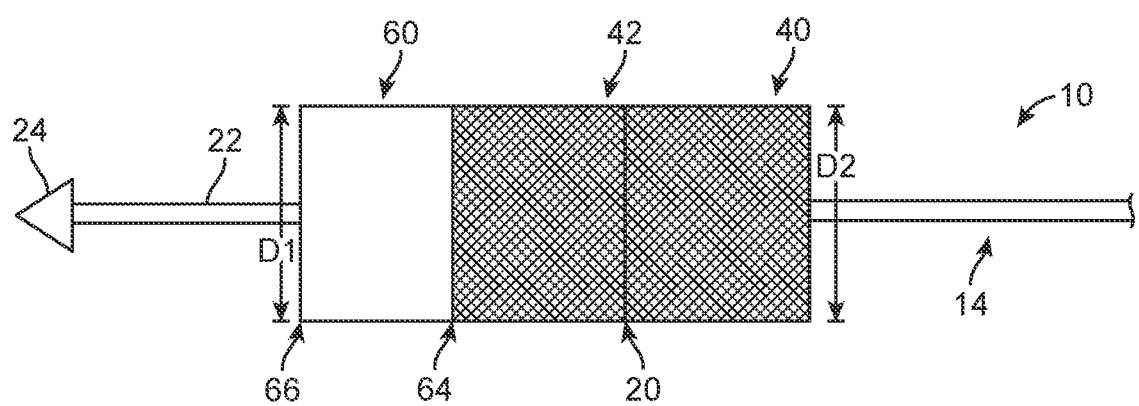
FIG. 3B is a schematic illustration of part of the delivery device of FIG. 3A having the stent frame in the expanded arrangement and the wrap in the delivery position.

FIG. 2 illustrates, in detail, the non-limiting prosthetic valve 40 useful with systems and methods of the present disclosure. As a point of reference, the prosthetic valve 40 has a compressed, delivery configuration as is schematically illustrated in FIG. 3A. The prosthetic valve 40 also has a normal, expanded arrangement as is shown in FIGS. 2 and 3B, for example. The prosthetic valve 40 includes a stent frame 42 and a valve structure 48. The stent frame 42 is generally tubular and has first and second ends 44, 46 and can assume any of the forms described herein, and is generally constructed so as to be self-expandable from the compressed arrangement of FIG. 3A to the normal, expanded deployed arrangement of FIGS. 2 and 3B. In other embodiments, the stent frame 42 is expandable to the expanded arrangement by a separate device (e.g., a balloon internally located within the stent frame 42). The valve structure 48 is assembled to the stent frame 42 and provides two or more (typically three) leaflets 50. The valve structure 48 can assume any of the forms described herein, and can be assembled to the stent frame 42 in various manners, such as by sewing the valve structure 48 to the stent frame 42.

The disclosed prosthetic valve 40, which may be of many configurations as discussed herein, includes a paravalvular leakage prevention and/or mitigation wrap 60 (schematically illustrated and shown apart from the prosthetic valve in FIG. 2 for ease of illustration). In some embodiments, the wrap 60 comprises a body 62 made of a thin metal mesh material, such as Nitinol™ mesh, a braided or laser cut elastomer such as polyurethane, C-FLEX® biomedical tubing available from Saint-Gobain North America, Malvern, Pennsylvania, silicone or a braided metal such as platinum iridium or cobalt chromium, for example. The body 62 can also be constructed of more than one material, for example, the body 62 can also include fabric, tissue (e.g., autologous tissue, xenograph material, treated pericardium, porcine, bovine, or equine tissue) or bioabsorbable mesh (e.g., poly (glycerol-co-sebacate), polylactic acid and polycaprolactone).

Figure 3C:
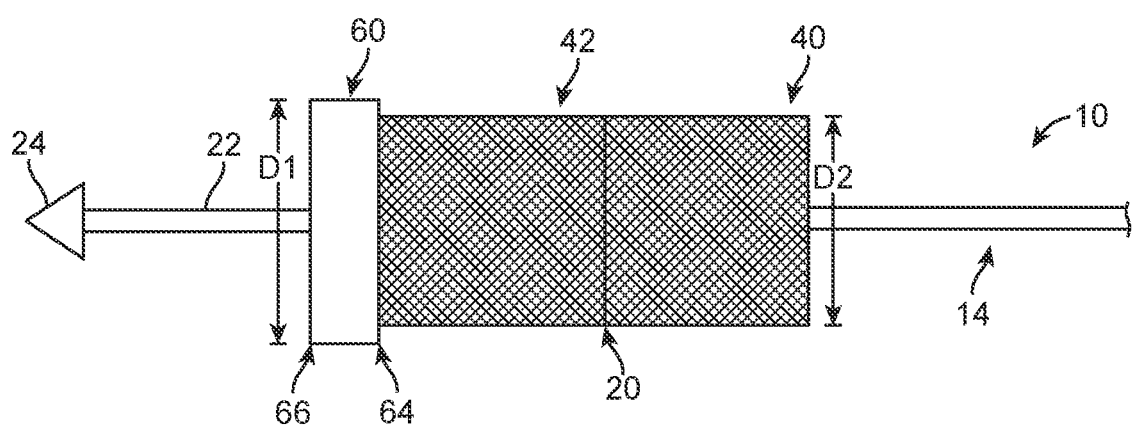
FIG. 3C is a schematic illustration of part of the delivery device of FIGS. 3A-3B having the stent frame in the expanded arrangement and the wrap in a deployed position.

The prosthetic valve 40 is configured so that the wrap 60 can be selectively deployed independent of the arrangement of the stent frame 42. For example, FIG. 3A schematically illustrates the stent frame 42 in a delivery arrangement in which the wrap 60 is in the delivery position and has approximately the same diameter as the stent frame 42, wherein the wrap diameter D1 is measured as a greatest distance between any two opposing points of the wrap 60. Turning now also to FIG. 3B, which illustrates the stent frame 42 in the expanded arrangement in which the wrap 60 has not yet been deployed. Therefore, in FIG. 3B the diameter D2 of the stent frame 42 is approximately the same as the diameter D1 of the wrap 60. In one exemplary deployment position, as illustrated in FIG. 3C, a first end 64 of the wrap 60 is moved toward a second end 66 of the wrap 60 causing the wrap 60 to bulge outwardly, thereby expanding the diameter D1 of the wrap 60 so that the diameter D1 of the wrap 60 is greater than the diameter D2 of the stent frame 42 (see also, FIGS. 5A-5D). In an alternate deployment position, illustrated in FIG. 3D, the second end 66 of the wrap 60 is moved toward the first end 64 to cause the wrap 60 to bulge outwardly, also resulting in the diameter D1 of the wrap 60 being greater than the diameter D2 of the stent frame 42 to mitigate or stop paravalvular leakage at a native heart valve.

Figure 4A:
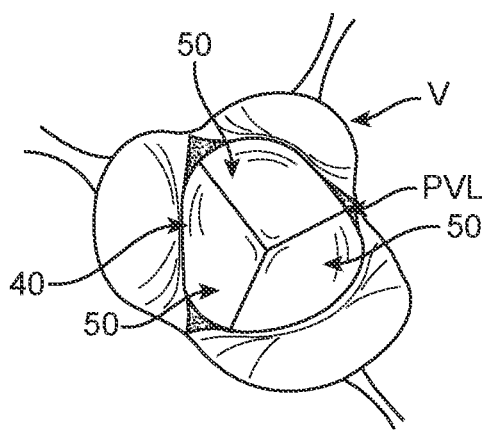
FIG. 4A is a partial, schematic profile view of the stented prosthetic heart valve of FIG. 2 deployed at a native heart valve with the wrap (not visible) in the delivery position; wherein paravalvular leakage is occurring around the stented prosthetic heart valve.
Figure 4B:
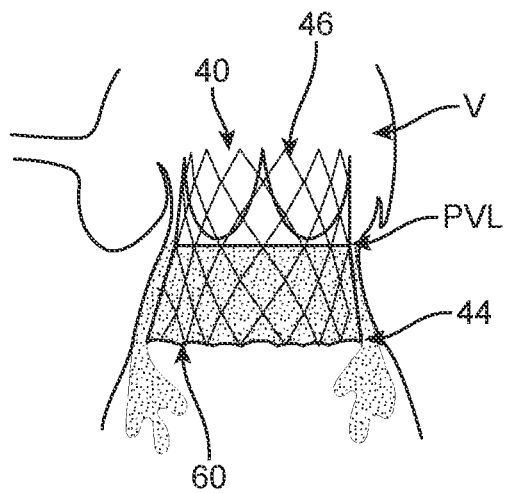
FIG. 4B is a schematic side view of the stented prosthetic heart valve of FIG. 4A deployed at the native heart valve; wherein paravalvular leakage is occurring around the stented prosthetic heart valve and the wrap, which is in the delivery position.

The delivery device 10 and prosthetic valve 40 configurations disclosed herein are beneficial in that the diameter D1 of the wrap 60 can be selectively enlarged in situ. In this way, the clinician has the option of whether or not to deploy the wrap 60 based on the occurrence or lack of paravalvular leakage after the prosthetic valve 40 is deployed at a native heart valve V. For example, see FIGS. 4A-4B illustrating the deployed prosthetic valve 40 having the wrap 60 that has not yet been deployed. Paravalvular leakage PVL is occurring between the prosthetic valve 40 and the native valve V so it is likely that a clinician would opt to deploy the wrap 60 upon detection of the leakage PVL. If no paravalvular leakage is detected upon deployment of the prosthetic valve 40, the wrap 60 can be left in the first, delivery position in which the wrap 60 generally conforms to the stent frame 42.

FIGS. 5A-5D further illustrate the variable diameter D1 of the wrap 60. As noted above, the wrap 60 is configured to have a delivery position (FIGS. 5A-5B) and a deployed position (FIGS. 5C-5D) in which the diameter D1 of the wrap 60 increases as the wrap 60 bulges outwardly. In one illustrative embodiment, a maximum distance D3 that the wrap 60 bulges out from the stent frame 42 in the deployed position of FIGS. 5C-5D is about 3 mm to about 4 mm.

Actuating selective movement of the wrap 60 from the delivery position of FIGS. 5A-5B to the deployed position of FIGS. 5C-5D can be accomplished in a variety of ways. In one such way, as generally depicted in FIGS. 6A-6B, the delivery device 10 includes a plurality of tethers 26 (e.g., three), such as cables, wires, sutures, chords, filaments, or tension members, that interconnect the tip 24 and the wrap 60. The tethers 26 can be routed inside the stent frame 42, outside the stent frame 42, or a combination of inside and outside the stent frame 42. In this embodiment, each tether 26 has a first end 28*a* secured to the tip 24 and a second end 28*b* secured to a second end 66 of the wrap 60 (only end of one tether 26 are referenced for ease of illustration). The delivery device 10 can be configured to have the second end 66 of the wrap 60 movable toward the first end 64 of the wrap 60, which is fixed to the stent frame 42. In this embodiment, deployment of the wrap 60 is actuated by proximally retracting the tip 24 past the second end 66 of the wrap 60 so that the second end 66 is brought closer to the first end 64, thus causing the wrap 60 to bulge outwardly. In further alternate embodiments which function and are operated similarly, the tether(s) 26 are secured to other locations on the shaft assembly 14.

An alternate configuration and method of selectively actuating the wrap 60 is shown in FIGS. 7A-7B. In this embodiment, the first end 28a of each tether 26 is secured to the tip 24 and the second end 28b is secured to the first end 64 of the wrap 60 (only end of one tether 26 are referenced for ease of illustration). The tethers 26 can be routed inside the stent frame 42, outside the stent frame 42, or a combination of inside and outside the stent frame 42, as desired. The distal end 66 of the wrap is secured to the stent frame 42. Movement of the wrap 60 from the delivery position (FIG. 7A) to the deployed position (FIG. 7B) is actuated by pushing the tip 24 distally. As best seen in FIG. 7B, actuation of the wrap 60 is caused by extending the delivery device 10 further into the ventricle outflow tract T, past the second end 46 of the prosthetic valve 40, thus pulling the tethers 26 distally to subsequently pull the first end 64 of the wrap 60 toward the second end 66. In further alternate embodiments which function and are operated similarly, the tether(s) 26 are secured to other locations of the shaft assembly 14.

Once the wrap 60 is maintained in the deployed position via any of the various methods disclosed herein and the prosthetic valve 40 hemodynamics and paravalvular leakage are assessed and deemed acceptable, the delivery device 10 is disengaged from the wrap 60 and the prosthetic valve 40 so that the delivery device 10 can be retracted from the patient. In one embodiment, illustrated in FIGS. 8A-8B, the wrap 60 includes one or more apertures 68 through which a respective one of one or more tethers 126 is threaded. A first end (see also FIGS. 6A-7B) of each tether 126 is secured to the delivery device 10 and a second end 128 of each tether 126 forms a flexible pigtail curve 150 that is sufficiently rigid to maintain the respective tether 126 to the wrap 60 as the wrap 60 is pulled into the deployed position of FIGS. 6B and 7B. After the wrap 60 is deployed, each tether 126 remains positioned within the aperture 68 unless sufficient pulling force is provided by the delivery device 10 via the shaft assembly 14 to straighten the pigtail curve 150 so that the tether 126 can be pulled through the aperture 68 to disengage from the wrap 60. All tethers 126 can be similarly configured or can have different configurations.

A similar alternate tether 226 that can be incorporated into a delivery device (e.g., the delivery device 10 of FIGS. 1 and 6A-7B) is illustrated in FIGS. 9A-9B. In this embodiment, a first end (see also FIGS. 6A-7B) of each tether 226 is secured to the delivery device 10 (e.g., to the tip 24 or elsewhere) and a second end 238 of the tether 226 includes a compressible section 250 that is sufficiently rigid to maintain the respective tether 226 within an aperture 68 of the wrap 60 as the wrap 60 is pulled into the deployed position (FIGS. 6B and 7B). After the wrap 60 is deployed, the tether 226 remains positioned within the aperture 68 of the wrap 60 unless sufficient pulling force is provided by the delivery device 10 (e.g., via the handle assembly 16) to compress the compressible section 250 within the aperture 68 so that the tether 226 can be pulled through the aperture 68 to disengage from the wrap 60.

As generally depicted in FIGS. 10A-10B, an alternate configuration and method of selectively actuating the wrap 60 comprises having one end 28b of each tether secured to the second end 66 of the wrap 60 and the other end (not visible) of each tether 26 extends through a portion of the stent frame 42 proximal of the second end 66 and then extend distally to a respective opening 25 in the delivery device tip 24 or other portion of the shaft assembly 14 and then extends proximally through the shaft assembly 14 to handle assembly 16 (see also FIG. 1), wherein handle assembly 16 is configured to tension or shorten the length of each tether 26 in a proximal direction to deploy the wrap 60 as shown in FIG. 10B. As with prior embodiments, the tethers 26 can be routed inside the stent frame 42, outside the stent frame 42, or a combination of inside and outside the stent frame 42. Once the wrap 60 has been deployed, the tethers 26 can be removed from the wrap 60 via a variety of methods. For example, one end of each tether 26 can be released and the entirety of the tether 26 can be withdrawn from the patient. Alternatively, the tethers 26 can be cut from the delivery device 10 and left within the patient or released in other ways discussed above.

Similar to that described with respect to FIGS. 6A-6B and 10A-10B, a further alternate configuration and method of selectively actuating the wrap 60 comprises having one end 28b of each tether 26 secured to the first end 64 of the wrap 60 and the other end (not visible) of each tether 26 extends distally to a respective opening 25 in the delivery device tip 24 or other portion of the shaft assembly 14 and then extends proximally through the shaft assembly 14 to the handle assembly 16 (see also, FIG. 1). The handle assembly 16 is configured to tension or shorten the length of each tether 26 in a proximal direction to deploy the wrap 60 to a position substantially similar to what is shown in FIG. 7B. As desired, the tethers 26 can be routed inside the stent frame 42, outside the stent frame 42, or a combination of inside and outside the stent frame 42. Once the wrap 60 has been deployed, the tethers 26 can be removed from the wrap 60 in ways discussed above, for example. In further alternate configurations and methods (not shown) of selectively actuating the wrap 60 comprises having each tether 26 loop through one end of the wrap 60 while both ends of each tether 26 extend back to the handle assembly 16, wherein the handle assembly 16 can tension or shorten the length of each tether 26 in a proximal direction to deploy the wrap 60. Once the wrap 60 has been deployed, the tethers 26 can be removed from the wrap 60 in any of the ways discussed above, for example.

To maintain the wrap 60 of any of the disclosed embodiments in the deployed position, the stent frame 42 and/or the wrap 60 can include one or more coupling elements 70 such as a ratchet system or the like. As is generally illustrated in FIGS. 11A-11E one such coupling element or ratchet system 70 includes at least one forward facing barb 72a connected to the stent frame 42 and angled toward the first end 44 of the stent frame 42. Also proximate the first end 44 of the stent frame 42 is a reverse barb 72b that is angled either perpendicular from the stent frame 42 or toward the second end 46 of the stent frame 42. As the wrap 60 is deployed by the delivery device 10, in this embodiment, the tether 26 is pulling the first end 64 of the wrap 60 toward the second end 66, over the forward facing barb(s) 72a. If the force applied to the wrap 60 is greater than the force required to release the tether 26, the tether 26 will release from the wrap 60. Otherwise, the reverse barb 72b will force the release of the tether 26 from the wrap 60 by restricting further movement of the tether 26 in the proximal direction, thus increasing tension on the tether 26. When the wrap 60 contacts the reverse barb 72b and is pulled in the direction therepast, the tension on the tether 26 increases, thereby releasing the tether 26. A hook (not shown) or other similar structure can be arranged on the stent frame 42 to function in a similar fashion as the reverse barb 72b. Once the wrap 60 released from the tether 26, the forward facing barbs 72a maintain the wrap 60 in the deployed position of FIGS. 6B, 7B, 10B and 11E. If the wrap 60 is to be deployed, the tethers 26 are moved proximally as illustrated in FIG. 11B. During this process, if there are gaps between the stent frame 42 and the patient's anatomy (see also, FIG. 4A), the wrap 60 ratchets proximally down the stent frame 42, billowing out and filling those gaps, if there are no gaps between the stent frame 42 and the patient's anatomy, then the wrap 60 does not billow out and cannot ratchet down the stent frame 42. During this process, the force required to move the wrap 60 is configured to be greater than the force required to release the tether 26 so that the tether(s) 26 releases from the wrap 60. If the force required to move the wrap 60 is less than that to release the tether 26 from the wrap 60, the reverse barb 72b will force the release of the tether 26 from the wrap 60 when the wrap 60 is pulled in a direction of the second end 66. This function highlights the importance of the reverse barb 72b that ensures that, when tethers 126, 226 are used as illustrated in FIGS. 8A-9B, for example, the pigtail curves 150 or compressible sections 228 uncouple the respective tether 126, 266 from the wrap 60 before the wrap 60 is pulled below the second end 66 of the stent frame 42. In this embodiment, the wrap 60 can include a ring or other attachment 78 configured to engage the barbs 72a, 72b. The wrap 60 can also include a second ring 80 at the second end, if desired. It is noted that the ratchet system 70 can be oriented in the opposite direction on the stent frame 42 when the wrap 60 is configured to move proximally into the deployed position as discussed with respect to FIG. 6A-6B or 10A-10B, for example. The ratchet system 70, if oriented in the opposite direction on the stent frame 42, could be configured to function in a similar manner to maintain the wrap 60 in the deployed position.

Figure 3D:
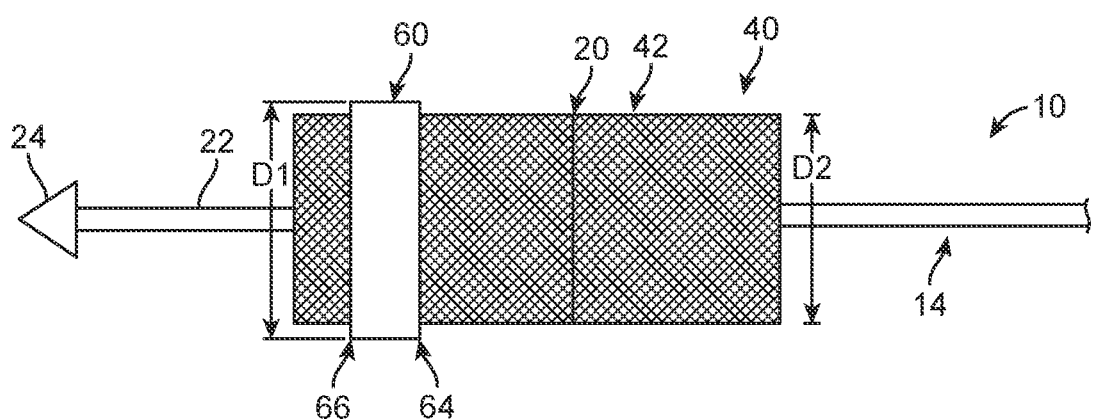
FIG. 3D is a schematic illustration of part of the delivery device of FIGS. 3A-3C having the stent frame in the expanded arrangement and the wrap in an alternate deployed position.

In further alternate embodiments, the prosthetic valve 40 includes an alternate wrap 160 that self-transitions from a delivery position (FIG. 12A) to a deployed position (FIG. 12B). This self-transitioning function is provided by a plurality of flexible spines 180 spaced about the wrap 160 between first and second ends 164, 166. The spines 180 are configured to be biased into the form of FIG. 12B. Therefore, if both of the first or second ends 164 or 166 of the wrap 160 are secured to the stent frame 42 and then one of those ends 164 or 166 is released from the stent frame 42, the wrap 160 will naturally flex and bow outwardly to the deployed position of FIG. 12B due to the biasing force of the spines 180. In this embodiment, the spines 180 can optionally include apertures 182 at the movable end (e.g., the first end 164, however the second end 166 could be the movable end as generally depicted in FIG. 3D) through which an elongate tension member 120 can be threaded as shown in FIG. 12C. The tension member 120 can optionally be utilized with the delivery device 10 to compress the prosthetic valve (not shown, see also FIGS. 2-3A) and can also be released from the prosthetic valve 40 by the delivery device 10, without the need for tethers 26 (see also, e.g., FIGS. 6A-7B), to deploy the wrap 160 as once the tension member 120 interconnecting the first, movable end 164 to the stent frame 42 (see also FIGS. 6A-7B) is released, the wrap 160 naturally transitions to the deployed position of FIG. 12B.

In alternate embodiments, largely similar to that of FIGS. 12A-12C, a body 162 of the wrap 160 can be made of a memory shape material so that the biased deployment arrangement of FIG. 12B is achieved and maintained with only the body 162 itself (i.e. the spines 180 can optionally be omitted). In such an embodiment, one of the first and second ends 164, 166 of the wrap 160 is releasably secured with the tension member 120 or the like to the stent frame 42 while the other opposing end 164 or 166 is secured to the stent frame 42. Once the releasably connected end 164 or 166 is released from the stent frame 42, the wrap 160 will naturally transition to its biased form, which is configured to bulge outwardly similar to previously disclosed embodiments (see FIG. 12B as one example).

As referred to herein, stented prosthetic heart valves or prosthetic valves 40 that can be modified to incorporate wraps (e.g., wraps 60, 160) disclosed above and delivered and deployed with devices and methods of the present disclosure may assume a wide variety of different configurations. For example, the prosthetic heart valves can be a biostented prosthetic heart valve having tissue leaflets or a synthetic heart valve having polymeric, metallic, or tissue-engineered leaflets, and can be specifically configured for replacing any heart valve. Thus, the prosthetic valves 40 can be generally used for replacement of a native aortic, mitral, pulmonic, or tricuspid valve, for use as a venous valve, or to replace a failed bioprosthesis, such as in the area of an aortic valve or mitral valve, for example.

In general terms, the stents or stent frames 42 of the present disclosure are generally tubular support structures having an internal area in which valve structure 48 leaflets 50 will be secured. The leaflets 50 can be formed from a variety of materials, such as autologous tissue, homologous material, xenograph material, or synthetics as are known in the art. The leaflets may be provided as a homogenous, biological valve structure, such as porcine, bovine, or equine valves. Alternatively, the leaflets 50 can be provided independent of one another (e.g., bovine, porcine or equine pericardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic valves of the types described herein can incorporate more or less than three leaflets.

Some embodiments of the stent frame 42 can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached leaflets can be mounted onto a delivery device, (e.g., the delivery device 10). The stent frame support structures are configured so that they can be changed to their normal, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components.

The prosthetic valve 40 is configured for replacing an aortic valve. Alternatively, other shapes are also envisioned, adapted for the specific anatomy of the valve to be replaced (e.g., prosthetic valves in accordance with the present disclosure can alternatively be shaped and/or sized for replacing a native mitral, pulmonic, or tricuspid valve). Regardless, the valve structure 48 can be arranged to extend less than an entire length of the stent frame 42. In particular, the valve structure 48 can be assembled to, and extend along, the first end 44 of the prosthetic valve 40, whereas the second end 46 can be free of the valve structure 48 material. A wide variety of other constructions are also acceptable and within the scope of the present disclosure. For example, the valve structure 48 can be sized and shaped to extend along an entirety, or a near entirety, of a length of the stent frame 42.

Although the present disclosure has been described with reference to preferred embodiments, workers skilled in the art will recognize that changes can be made in form and detail without departing from the spirit and scope of the present disclosure.

What is claimed is:

1. A stented prosthetic heart valve comprising:
   a stent frame comprising a compressed arrangement for delivery within a vasculature and an expanded arrangement upon deployment within a native heart valve;
   valve leaflets disposed within and secured to the stent frame;
   a wrap comprising a first axial end and a second axial end opposite the first axial end; the wrap encircling the stent frame and formed of a flexible material; the wrap comprising a delivery position and a deployed position, wherein, in both the delivery and deployed positions the second axial end is distal to the first axial end; wherein the wrap can be actuated from the delivery position to the deployed position independently of the arrangement of the stent frame;
   the wrap is configured to achieve the deployed position by positioning one of the first axial end and the second axial end of the wrap axially closer to the other of the first axial end and the second axial end of the wrap such that a central portion of the wrap radially expands under axial compression to form an outward bulge in the deployed position without radially expanding the first axial end and without radially expanding the second axial end, wherein the outward bulge comprises a single outwardly facing convex surface segment encircling the stent frame and continuously extending from the first axial end to the second axial end; and
   a tether removably attached to the wrap, wherein the wrap is configured to achieve the deployed position to form the outward bulge by applying tension to the tether, and, wherein the tether extends through an opening in the wrap.

2. The stented prosthetic heart valve of claim 1, wherein the wrap comprises a coupling element; wherein the coupling element maintains a position of the first axial end of the wrap relative to the opposing second axial end of the wrap to maintain the outward bulge of the wrap in the deployed position.

3. The stented prosthetic heart valve of claim 1, wherein the wrap comprises the first axial end coupled to the stent frame and the second axial end not coupled to the stent frame, wherein a diameter of the wrap is configured to be selectively enlarged by axially moving the second axial end of the wrap closer to the first axial end of the wrap.

4. The stented prosthetic heart valve of claim 3, wherein the diameter of the wrap is configured to be selectively enlarged by axially moving the second axial end of the wrap axially closer to the valve leaflets.

5. The stented prosthetic heart valve of claim 1, wherein the outwardly facing convex surface segment comprises a toroidal surface segment.

6. The stented prosthetic heart valve of claim 1, wherein the wrap is configured to achieve the deployed position by positioning one of the first axial end and the second axial end of the wrap axially closer to the other of the first axial end and the second axial end of the wrap such that the wrap buckles under axial compression to form the outward bulge in the deployed position.

7. The stented prosthetic heart valve of claim 1, wherein an end of the tether includes a pigtail curve.

8. A stented prosthetic heart valve comprising:
   a stent frame comprising a compressed arrangement for delivery within a vasculature and an expanded arrangement upon deployment within a native heart valve;
   valve leaflets disposed within and secured to the stent frame;
   a wrap comprising a first axial end and a second axial end opposite the first axial end, wherein the second axial end is distal to the first axial end; the wrap encircling the stent frame and formed of a flexible material comprising a variable diameter defined by a greatest distance between any two opposing points on the wrap; wherein the wrap is configured to comprise a deployed position in which a diameter of the wrap can be selectively enlarged in situ;
   the wrap is configured to achieve the deployed position by positioning one of the first axial end and the second axial end of the wrap axially closer to the other of the first axial end and the second axial end of the wrap such that a central portion of the wrap radially expands under axial compression to form an outward bulge in the deployed position without radially expanding the first axial end and without radially expanding the second axial end; and
   a tether removably attached to the wrap, wherein the wrap is configured to achieve the deployed position to form the outward bulge by applying tension to the tether, and, wherein the tether extends through an opening in the wrap.

9. The stented prosthetic heart valve of claim 8, wherein the wrap comprises a coupling element; wherein the coupling element maintains a position of the first axial end of the wrap relative to the second axial end of the wrap to maintain the outward bulge of the wrap in the deployed position.

10. The stented prosthetic heart valve of claim 8, wherein the wrap comprises the first axial end coupled to the stent frame and the second axial end not coupled to the stent frame, wherein the diameter of the wrap is configured to be selectively enlarged by axially moving the second axial end of the wrap closer to the first axial end of the wrap.

11. The stented prosthetic heart valve of claim 10, wherein the diameter of the wrap is configured to be selectively enlarged by axially moving the second axial end of the wrap axially closer to the valve leaflets.

12. The stented prosthetic heart valve of claim 8, wherein the wrap comprises a delivery position, the diameter of the wrap is greater in the deployed position than in the delivery position, and the wrap can be actuated from the delivery position to the deployed position independently of the arrangement of the stent frame.

13. The stented prosthetic heart valve of claim 8, wherein the wrap is configured to achieve the deployed position by positioning one of the first axial end and the second axial end of the wrap axially closer to the other of the first axial end and the second axial end of the wrap such that the wrap buckles under axial compression to form the outward bulge in the deployed position.

14. The stented prosthetic heart valve of claim 8, wherein an end of the tether includes a pigtail curve.

15. The stented prosthetic heart valve of claim 8, wherein the outward bulge comprises a single outwardly facing convex surface segment encircling the stent frame and continuously extending from the first axial end to the second axial end.

16. The stented prosthetic heart valve of claim 15, wherein the outwardly facing convex surface segment comprises a toroidal surface segment.

\* \* \* \* \*